United States Patent
Wang et al.

(10) Patent No.: US 10,993,622 B2
(45) Date of Patent: May 4, 2021

(54) MOTION-ADAPTIVE INTERACTIVE IMAGING METHOD

(71) Applicant: LI-COR, Inc., Lincoln, NE (US)

(72) Inventors: Han-Wei Wang, Lincoln, NE (US);
Lyle R. Middendorf, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 474 days.

(21) Appl. No.: 15/819,603

(22) Filed: Nov. 21, 2017

(65) Prior Publication Data

US 2018/0140197 A1 May 24, 2018

Related U.S. Application Data

(60) Provisional application No. 62/425,967, filed on Nov. 23, 2016, provisional application No. 62/489,921, filed on Apr. 25, 2017.

(51) Int. Cl.
*A61B 5/00* (2006.01)
*H04N 5/232* (2006.01)
(Continued)

(52) U.S. Cl.
CPC ............ *A61B 5/0077* (2013.01); *A61B 6/481* (2013.01); *A61B 6/50* (2013.01); *G06T 1/0007* (2013.01);
(Continued)

(58) Field of Classification Search
None
See application file for complete search history.

(56) References Cited

U.S. PATENT DOCUMENTS 2,792,502 A  5/1957 O'Connor et al.
5,103,338 A  4/1992 Crowley et al.
(Continued)

FOREIGN PATENT DOCUMENTS

CN  101301192   11/2008
CN  101401722 A   4/2009
(Continued)

OTHER PUBLICATIONS

Choi et al., "A spatial-temporal multiresolution CMOS image sensor with adaptive frame rates for tracking the moving objects in region-of-interest and suppressing motion blur"., IEEE Journal of Solid-State Circuits, vol. 42, No. 12, 2007. (Year: 2007).*
(Continued)

*Primary Examiner* — Yi-Shan Yang
(74) *Attorney, Agent, or Firm* — Kilpatrick Townsend & Stockton LLP

(57) ABSTRACT

Methods and systems are provided for the detecting and presenting of faint signals from a real-time interactive imager. A real-time view of a subject is controlled by a user by entering commands that move the subject or a camera used to record the real-time view. The rate of this movement is monitored, and when the rate descends below a preset value, a trigger is sent to the camera. In response to the trigger, the camera switches to a lower frame frequency for capturing the real-time view of the subject, thereby increasing the amount of light collected in each frame, and increasing the sensitivity of the camera to faint signals. The methods and systems are particularly relevant for surgical or biopsy imaging, in which both a higher frame rate preview image of a subject for 3D visualization, and a higher sensitivity fluorescence image of the subject for tumor margin assessment, are desired.

17 Claims, 6 Drawing Sheets

(51) Int. Cl.
  *A61B 6/00* (2006.01)
  *H04N 5/235* (2006.01)
  *G06T 1/00* (2006.01)
(52) U.S. Cl.
  CPC ....... *H04N 5/2354* (2013.01); *H04N 5/23216* (2013.01); *H04N 5/23245* (2013.01); *H04N 5/23254* (2013.01); *H04N 5/23267* (2013.01)

(56) References Cited

U.S. PATENT DOCUMENTS

| | | |
|---|---|---|
| 5,224,141 A | 6/1993 | Yassa et al. |
| 5,408,294 A | 4/1995 | Lam |
| 5,782,762 A | 7/1998 | Vining |
| 5,812,265 A | 9/1998 | Hoshiyama |
| 5,959,295 A | 9/1999 | Braun |
| 6,165,170 A | 12/2000 | Wynne et al. |
| 6,172,373 B1 | 1/2001 | Hara et al. |
| 6,356,272 B1 | 3/2002 | Matsumoto et al. |
| RE37,913 E | 11/2002 | Nishi |
| 6,711,433 B1 | 3/2004 | Geiger et al. |
| 7,218,393 B2 | 5/2007 | Sharpe et al. |
| 7,286,232 B2 | 10/2007 | Bouzid et al. |
| 7,453,456 B2 | 11/2008 | Petrov et al. |
| 7,505,124 B2 | 3/2009 | Kreckel et al. |
| 7,551,711 B2 | 6/2009 | Sarment et al. |
| 7,715,523 B2 | 5/2010 | Lafferty et al. |
| 7,929,743 B2 | 4/2011 | Khorasani et al. |
| 8,115,918 B2 | 2/2012 | Zavislan et al. |
| 8,220,415 B2 | 7/2012 | Lamb et al. |
| 8,503,602 B2 | 8/2013 | Lafferty et al. |
| 8,741,232 B2 | 6/2014 | Baysal et al. |
| 8,754,384 B1 | 6/2014 | Persoon et al. |
| 8,848,071 B2 * | 9/2014 | Asakura ............ H04N 5/23245 348/222.1 |
| 8,851,017 B2 | 10/2014 | Lamb et al. |
| 8,892,192 B2 | 11/2014 | Cuccia et al. |
| 9,053,563 B2 | 6/2015 | Embrey et al. |
| 9,345,389 B2 | 5/2016 | Nie et al. |
| 9,528,938 B2 | 12/2016 | Wang |
| 9,557,281 B2 | 1/2017 | Yang et al. |
| 9,632,187 B2 | 4/2017 | Poon et al. |
| 10,254,227 B2 | 4/2019 | Wang |
| 10,278,586 B2 | 5/2019 | Wang |
| 10,489,964 B2 | 11/2019 | Wang |
| 10,948,415 B2 | 3/2021 | Wang |
| 2002/0012420 A1 | 1/2002 | Bani-Hashemi et al. |
| 2003/0078477 A1 | 4/2003 | Kang et al. |
| 2004/0101088 A1 | 5/2004 | Sabol et al. |
| 2005/0046840 A1 | 3/2005 | Kusuzawa et al. |
| 2005/0227374 A1 | 10/2005 | Cunningham et al. |
| 2006/0072123 A1 | 4/2006 | Wilson et al. |
| 2006/0250518 A1 | 11/2006 | Nilson et al. |
| 2006/0253035 A1 | 11/2006 | Stern |
| 2007/0121099 A1 | 5/2007 | Matsumoto et al. |
| 2007/0276184 A1 | 11/2007 | Okawa |
| 2008/0025475 A1 | 1/2008 | White |
| 2008/0077019 A1 | 3/2008 | Xiao et al. |
| 2008/0297890 A1 | 12/2008 | Natori et al. |
| 2008/0312540 A1 | 12/2008 | Ntziachristos |
| 2009/0011386 A1 | 1/2009 | Eiff et al. |
| 2009/0018451 A1 | 1/2009 | Bai et al. |
| 2009/0032731 A1 | 2/2009 | Kimura et al. |
| 2009/0129543 A1 | 5/2009 | Le Gros et al. |
| 2009/0192358 A1 | 7/2009 | Jaffer et al. |
| 2009/0208072 A1 | 8/2009 | Seibel et al. |
| 2009/0234225 A1 | 9/2009 | Martin et al. |
| 2009/0250631 A1 | 10/2009 | Feke et al. |
| 2009/0268010 A1 * | 10/2009 | Zhao ............ A61B 1/0638 348/45 |
| 2010/0309548 A1 | 12/2010 | Power |
| 2011/0025880 A1 | 2/2011 | Nandy |
| 2011/0104071 A1 | 5/2011 | Lee et al. |
| 2011/0116694 A1 | 5/2011 | Gareau et al. |
| 2011/0135190 A1 | 6/2011 | Maad |
| 2011/0229023 A1 | 9/2011 | Jones et al. |
| 2012/0049087 A1 | 3/2012 | Choi et al. |
| 2012/0049088 A1 | 3/2012 | Klose |
| 2012/0065518 A1 | 3/2012 | Mangoubi et al. |
| 2012/0105600 A1 | 5/2012 | Meyer et al. |
| 2012/0182411 A1 | 7/2012 | Nakatsuka et al. |
| 2012/0194663 A1 | 8/2012 | Haisch et al. |
| 2012/0206448 A1 | 8/2012 | Embrey |
| 2012/0206577 A1 | 8/2012 | Guckenberger et al. |
| 2012/0257079 A1 * | 10/2012 | Ninan ................ H04N 5/2355 348/222.1 |
| 2012/0302880 A1 | 11/2012 | Tian et al. |
| 2012/0312957 A1 | 12/2012 | Loney et al. |
| 2013/0027516 A1 | 1/2013 | Hart et al. |
| 2013/0057673 A1 | 3/2013 | Ferrer Moreu et al. |
| 2013/0135081 A1 | 5/2013 | McCloskey et al. |
| 2014/0125790 A1 | 5/2014 | Mackie et al. |
| 2014/0140594 A1 | 5/2014 | Mahadevan-Jansen et al. |
| 2014/0163388 A1 | 6/2014 | Sasayama et al. |
| 2014/0186049 A1 * | 7/2014 | Oshima ............ H04B 10/1143 398/118 |
| 2014/0276008 A1 | 9/2014 | Steinbach et al. |
| 2014/0294247 A1 | 10/2014 | Sirault et al. |
| 2014/0346359 A1 | 11/2014 | Holliday |
| 2014/0349337 A1 | 11/2014 | Dasari et al. |
| 2014/0378843 A1 | 12/2014 | Valdes et al. |
| 2015/0000410 A1 | 1/2015 | Grimard et al. |
| 2015/0008337 A1 | 1/2015 | Shimizu |
| 2015/0018690 A1 * | 1/2015 | Kang .................... A61B 5/418 600/473 |
| 2015/0022824 A1 | 1/2015 | Cadent et al. |
| 2015/0062153 A1 | 3/2015 | Mihalca et al. |
| 2015/0073213 A1 | 3/2015 | Khait et al. |
| 2015/0098126 A1 | 4/2015 | Keller et al. |
| 2015/0105283 A1 | 4/2015 | Hollman-Hewgley et al. |
| 2015/0257653 A1 * | 9/2015 | Hyde ................ A61B 5/021 600/473 |
| 2015/0359413 A1 | 12/2015 | David |
| 2015/0373293 A1 * | 12/2015 | Vance ................ H04N 5/4401 348/143 |
| 2016/0155472 A1 * | 6/2016 | Elg ................ H04N 5/23245 386/223 |
| 2016/0187199 A1 | 6/2016 | Brunk et al. |
| 2016/0217609 A1 | 7/2016 | Kornilov et al. |
| 2016/0245753 A1 | 8/2016 | Wang |
| 2016/0335984 A1 | 11/2016 | Wu |
| 2016/0377545 A1 | 12/2016 | Wang |
| 2017/0020627 A1 * | 1/2017 | Tesar .................... A61B 90/20 |
| 2017/0059487 A1 | 3/2017 | Wang |
| 2017/0176338 A1 | 6/2017 | Wu et al. |
| 2017/0309063 A1 | 10/2017 | Wang |
| 2017/0336706 A1 | 11/2017 | Wang |
| 2017/0367582 A1 | 12/2017 | Wang |
| 2018/0020920 A1 | 1/2018 | Ermilov et al. |
| 2018/0140197 A1 | 5/2018 | Wang et al. |
| 2018/0180550 A1 | 6/2018 | Franjic et al. |
| 2018/0209924 A1 | 7/2018 | Sasazawa et al. |
| 2018/0228375 A1 * | 8/2018 | Kim .................... A61B 5/0071 |
| 2018/0242939 A1 | 8/2018 | Kang et al. |
| 2019/0079010 A1 | 3/2019 | Bawendi et al. |
| 2019/0298303 A1 * | 10/2019 | Bingley .................. A61B 8/54 |

FOREIGN PATENT DOCUMENTS

| | | |
|---|---|---|
| CN | 101460953 A | 6/2009 |
| CN | 101984928 A | 3/2011 |
| CN | 102048525 | 5/2012 |
| CN | 203677064 U | 7/2014 |
| CN | 103082997 | 10/2015 |
| DE | 102011104216 | 12/2012 |
| EP | 2455891 | 5/2012 |
| GB | 2514125 | 11/2014 |
| JP | 02304366 | 12/1990 |
| JP | 0924052 A | 1/1997 |
| JP | 09236755 | 9/1997 |
| JP | 10123054 | 5/1998 |
| JP | 2000304688 A | 11/2000 |
| JP | 2004531729 | 10/2004 |

(56) References Cited

FOREIGN PATENT DOCUMENTS

| | | |
|---|---|---|
| JP | 2008298861 A | 12/2008 |
| JP | 2009008739 A | 1/2009 |
| JP | 2013253983 A | 12/2013 |
| JP | 6585728 B2 | 9/2019 |
| KR | 20130096910 | 9/2013 |
| WO | 2006113908 | 10/2006 |
| WO | 2007030424 | 3/2007 |
| WO | 2009115061 | 9/2009 |
| WO | 2013166497 | 11/2013 |
| WO | 2014094142 | 6/2014 |
| WO | 2015023990 | 2/2015 |
| WO | 2016014252 | 1/2016 |
| WO | 2016073569 | 5/2016 |
| WO | 2016100214 | 6/2016 |
| WO | 2016137899 | 9/2016 |
| WO | 2016210340 | 12/2016 |
| WO | 2017184940 | 10/2017 |
| WO | 2017200801 | 11/2017 |
| WO | 2017223378 | 12/2017 |
| WO | 2018098162 | 5/2018 |

OTHER PUBLICATIONS

U.S. Appl. No. 15/494,088, "Notice of Allowance," dated Sep. 18, 2019, 10 pages.
JP2017-562263, "Office Action," dated Mar. 3, 2020, 11 pages.
U.S. Appl. No. 15/192,771, "Final Office Action", dated Jan. 8, 2019, 10 pages.
U.S. Appl. No. 15/630,776, "Notice of Allowance", dated Dec. 21, 2018, 7 pages.
EP16756129.9, "Extended European Search Report", dated Jan. 19, 2019, 14 pages.
EP16815434.2, "Partial Supplementary European Search Report", dated Jan. 29, 2019, 16 pages.
PCT/US2017/031740, "International Preliminary Report on Patentability", dated Nov. 29, 2018, 18 pages.
PCT/US2017/038860, "International Preliminary Report on Patentability", dated Jan. 3, 2019, 8 pages.
U.S. Appl. No. 15/352,427, "Non-Final Office Action", dated Sep. 4, 2018, 9 pages.
U.S. Appl. No. 15/352,427, "Notice of Allowance", dated Nov. 21, 2018, 6 pages.
EP application No. EP16756129.9, "Partial European Search Report", dated Oct. 29, 2018, 17 pages.
PCT application No. PCT/US2017/028769, "International Preliminary Report on Patentability", dated Nov. 1, 2018, 13 pages.
U.S. Appl. No. 15/192,771, "Notice of Allowance," dated Apr. 2, 2019, 8 pages.
U.S. Appl. No. 15/955,567, "Notice of Allowance," dated Apr. 2, 2019, 11 pages.
U.S. Appl. No. 15/049,970, "Notice of Allowability", dated Oct. 14, 2016, 4 pages.
EP16815434.2, "Extended European Search Report", dated May 16, 2019, 19 pages.
JP2017-544296, "Office Action", dated May 7, 2019, 5 pages.
Kleiner et al., "Classification of Ambiguous Nerve Fiber Orientations in 3D Polarized Light Imaging", Med Image Comput Comput Assist Interv., vol. 15, Pt 1, 2012, pp. 206-213.
PCT/US2016/018972, "International Preliminary Report on Patentability", dated Aug. 29, 2017, 7 pages.
PCT/US2017/062812, "International Preliminary Report on Patentability", dated Jun. 6, 2019, 7 pages.
CN201680037184.6, "Office Action," dated Oct. 24, 2019, 12 pages.
PCT/US2018/027978, "International Preliminary Report on Patentability," dated Nov. 7, 2019, 9 pages.
International Search Report for PCT/US2018/027978 dated Jul. 12, 2018, 5 pages.

Sturm et al., "CopyMe3D: Scanning And Printing Persons In 3D*", Medical Image Computing And Computer-Assisted Intervention—Miccai 2015: 18th International Conference, Munich, Germany, Sep. 3, 2013, pp. 405-414.
International Search Report dated Feb. 8, 2018, for corresponding PCT Appln No. PCT/US2017/062812, 4 pages.
"Arctec Eva Fast Handheld 3D Scanner for Professionals", http://www.artec3d.com/hardware/artec-evat/, retrieved from the internet Apr. 19, 2016, 6 pages.
"Optical Scatter Imaging System for Surgical Specimen Margin Assessment During Breast Conserving Surgery", Project Information NIH Research Portfolio Online Reporting Tools, Project No. 1R01CA192803-01, 2 pages.
Bioptics Inc., "BioVision Digital Specimen Radiography (DSR) System", Premarket Notification 510(k) Summary, prepared May 2009, 8 pages.
Fang et al., "Combined Optical and X-ray Tomosynthesis Breast Imaging", Radiology, vol. 258, No. 1, Jan. 2011, pp. 89-97.
Faxitron Bioptics LLC, "BioVision Surgical Specimen Radiography System", http://www.faxitron.com/medical/products/biovision.html, retrieved from the internet Apr. 26, 2016, 2 pages.
Faxitron Bioptics LLC, "PathVision", http://www.faxitron.com/medical/products/pathvision.html, retrieved from the internet Apr. 26, 2016, 2 pages.
Lamberts et al., "Tumor-specific uptake of fluorescent bevacizumab-IRDye800CW microdosing in patients with primary breast cancer: a phase I feasibility study", Clinical Cancer Research, Personalized Medicine and Imaging, American Association for Cancer Research, 2016, 41 pages.
Lee et al. "Fusion of coregistered cross-modality images using a temporally alternating display method", Medical & Biological Engineering & Computing, Springer, vol. 38, No. 2, Mar. 1, 2000, pp. 127-132.
International Search Report for PCT/US2016/018972 dated Jun. 23, 2016, 1 page.
International Search Report for PCT/US2016/039382 dated Sep. 13, 2016, 3 pages.
International Search Report for PCT/US2017/028769 dated Sep. 22, 2017, 2 pages.
International Search Report for PCT/US2017/031740 dated Sep. 19, 2017, 3 pages.
International Search Report for PCT/US2017/038860 dated Sep. 22, 2017, 3 pages.
Perkin Elmer, "Every Cancer Tells A Story If You Have The Tools To Read It", http://go.perkinelmer.com/webmail/32222/179460051/9c4865b118d5295e96e973a5b6c28bad, 2 pages.
Tomowave Laboratories, "Imaging Modules", retrieved from the internet http://www.tomowave.com/imagingmodules.html, 1 page.
Wu et al., "Rotational imaging optical coherence tomography for full-body mouse embryonic imaging", Journal of Biomedical Optics, vol. 21, No. 2, Feb. 2016, pp. 026002-1-026002-9.
Badawi et al., Real-Time Tissue Assessment During Surgical Procedures, UC David Office of Research, Tech ID: 24307.
Orpheus Medical, Clinical Video Management and Visible Light Documentation, Slideshow dated Feb. 3, 2016. The Examiner's attention is directed to slide 11.
CN201680037184.6, "Office Action," dated Mar. 27, 2020, 21 pages.
EP16815434.2, "Office Action", dated Apr. 23, 2020, 6 pages.
Application No. EP17721277.6, Office Action, dated Jun. 18, 2020, 6 pages.
Application No. CN201680037184.6, Office Action, dated Sep. 21, 2020, 10 pages.
U.S. Appl. No. 16/359,852, Notice of Allowance, dated Feb. 18, 2021, 7 pages.
U.S. Appl. No. 16/529,463, Notice of Allowance, dated Jan. 25, 2021, 11 pages.
Mondal et al., "Real-Time Fluorescence Image-Guided Oncologic Surgery," Advances in Cancer Research, vol. 123, Available Online At: https://www.ncbi.nlm.nih.gov/pmc/articles/PMC4245053/pdf/nihms-643557.pdf, 2014, 37 pages.

* cited by examiner

MOTION-ADAPTIVE INTERACTIVE IMAGING METHOD

CROSS-REFERENCES TO RELATED APPLICATIONS

The present application claims the benefit of U.S. Provisional Patent Application No. 62/425,967, filed Nov. 23, 2016, and U.S. Provisional Patent Application No. 62/489,921, filed Apr. 25, 2017, the full disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

The success of oncologic surgery can depend on obtaining negative tumor margins so that no tumor tissues are left behind. Tumor margins are the healthy tissue surrounding the tumor, and more specifically, the distance between the tumor tissue and the edge of the surrounding tissue removed along with the tumor. Ideally, the margins are selected so that the risk of leaving tumor tissue within the patient is low. The current clinical approach to tumor margin assessment involves circumferential analysis of a resected specimen using frozen sections in a lab during surgical time (Chambers et al. (2015) *Laryngoscope* 125:636; Byers et al. (1978) *Amer. J Surgery* 136:525). Tactile and visual measures are traditionally the only methods available in this sampling process. However, complex three-dimensional (3D) primary specimens are often difficult to manipulate and orient for full inspection and processing.

As a specific example, margin assessments based on frozen sectioning is difficult to implement on breast cancer specimens due to fatty tissues. X-ray imaging and gamma detection are thus used intraoperatively to estimate the border of a tumor by looking at contrasts from inserted biopsy markers such as clips, wires, or seeds which help locate the tumor mass (O'Kelly et al. (2016) *J. Surgical Oncology* 113:256). X-ray cabinet imagers used in surgical suites can give a two-dimensional (2D) projection view of a sample in the form of a snap shot. However the 3D localization of inserts within the sample can significantly benefit the assessment (Kopens (2014) *Amer. J. Roentgenology* 202:299; Ciatto et al. (2013) *Lancet Oncology* 14:583; Chagpar et al. (2015) *Amer. J. Surgery* 210:886). The alternative use of a real-time motion-controlled orientation and imaging of a sample, coupled with the use of periodic X-ray shots, can therefore be helpful in viewing samples from different directions efficiently in the surgical suite.

Fluorescence image-guided surgery and fluorescence image-guided margin assessment are emerging technologies taking advantage of recent developments of fluorescence dyes and tumor targeting imaging agents from translational and clinical research areas (Garland et al. (2016) *Cell Chem. Bio.* 23:122; Warram (2014) *Cancer Metastasis Rev.* 33:809). In recent years, several fluorescence imaging systems have been developed and commercialized for image-guided surgery (Zhu and Sevick-Muraca (2015) *British J. Radiology* 88:20140547; Chi et al. (2014) *Theranostics* 4:1072; D'Souza et al. (2016) *J. Biomed. Opt.* 21:80901). Some of these handheld and overhead devices have been tested for use in the margin assessment of tumors, rather than for their well-established purpose of imaging primary tumor tissues. When used in situ with an image-guided systems above the wound bed, there exist significant ambient interferences such as those associated with broadband ambient light, wound bed fluids, and electro-magnetism. These interferences, along with a fluorescence imaging requirement of a high frame rate, together produce reduced detection limits or sensitivities of the devices. One approach to avoiding ambient light interferences without dimming operating room lights is the use of modulation of excitation light away from ambient frequencies. Alternatively, a cabinet biopsy imager (U.S. Patent Application No. 2016/0245753) can be used to isolate a sample from ambient interferences to provide a higher sensitivity.

The sensitivity of an imaging system is particularly important for margin assessment when a micro-extension of tumor tissue can reverse a negative result. In addition, microdose administration of imaging agents, and low concentration of cellular receptors of dye conjugates, would also demand high sensitivity of fluorescence detection of the imaging system. Several aspects of imaging have been identified as targets for improving signal sensitivity in fluorescence systems, including optimization of fluorescence excitation sources and emission filters, improvement of light collection efficiency, elimination of ambient light interferences, modification of the image sensor, and suppression of system noises. While each of these can positively influence the sensitivity of fluorescence imaging, they can also negatively influence the video-rate performance of image-guided systems.

Video rate or high-frame rate imaging, often with reflected white light, offers real-time viewing capability of a subject such as a surgical patient or tumor biopsy sample. Multichannel co-registration of this reflected white light image with a fluorescent image can produce an overlaid image useful in tumor assessment. However, the typical performance characteristics of these overlays of reflective light and fluorescence images sacrifices real-time motion sensitivity as a compromise to boost fluorescence sensitivity. This is the case for systems with charge-coupled device (CCD), complementary metal-oxide-semiconductor (CMOS), electron-multiplied-CCD, or intensified-CCD sensors. In general, improvements to high frame rate imaging negatively impact the sensitivity of the imaging system by reducing signal collection time in each frame as well as by reducing data processing time and increasing read noises of the imaging sensor.

BRIEF SUMMARY

In general, provided herein are imaging technology methods, computer programs, and systems for viewing a subject from multiple angles or orientations while adapting in real-time the imaging quality and imaging function in response to motion. The provided methods and systems maintain the capability of providing a real-time preview during image-guided navigation, while also including high-sensitivity image properties when an adaptive function is turned on. Motion-sensitive feedback from, for example, the movement of an imager, is used to assess user-controlled motion commands. When motion is substantially reduced or stopped, the imager is switched to an adaptive or enhanced configuration that can include additional imaging modalities, enhanced image quality, longer integration time for a better sensitivity, overlapping of channels, noise filtering, color changes, computational results, or other alterations. In this way, the adaptive imaging configuration can allow for better detection of faint signals at the location of interest that would otherwise be difficult to appreciate with the original imaging properties in use during the real-time preview and prior to the motion-adaptive switch.

For example, the capability to interactively review a sample in a 3D real-time image, with an optimal fluorescence imaging sensitivity adaptively triggered in response to a change in motion, has great potential for providing important information for the vetting of surgical samples. Furthermore, adaptive functional imaging with modalities of X-ray and high-sensitivity fluorescence imaging can significantly increase the efficiency, reduce the sampling error, and increase the diagnosis accuracy of intraoperative margin assessment in cancer surgery. Similarly, the utility of a biopsy imager can be improved by providing an interactive preview of a specimen with useful additional information enabled by adaptive imaging modalities.

One provided method for detecting and presenting faint signals from a real-time, interactive imager includes recording using a camera a first real-time view of a subject. The camera has a camera location and a camera orientation, and the subject has a subject location and a subject orientation. The camera also has a frame frequency, and the frame frequency when recording the first real-time view is a first frame frequency. The method further includes rendering for display the first real-time view. The method further includes changing the camera location or the camera orientation or the subject location or the subject orientation in response to an operator command. The method further includes monitoring a rate of movement in response to the operator command. The method further includes sending a trigger to the camera based upon the rate of movement descending below a target rate. The method further includes switching the frame frequency from the first frame frequency to a second frame frequency based on the trigger, wherein the second frame frequency is less than the first frame frequency. The method further includes capturing using the camera a second real-time view of the subject, wherein the frame frequency of the camera is the second frame frequency, thereby increasing an amount of light collected in each frame. The method further includes outputting for display the second real-time view.

In some embodiments, the camera captures fluorescence images of the subject. In some embodiments, the camera is a first camera, and a reflected white light real-time view is photographed with a second camera. In some embodiments, the camera records reflected white light images with the first frame frequency, and the camera captures fluorescence images with the second frame frequency. In some embodiments, the outputting includes overlaying a reflected white light image of the subject over the second real-time view of the subject, wherein the reflected white light image was recorded or photographed prior to the sending of the trigger.

In some embodiments, the recording of the first real-time view includes a first illumination of the subject, and the capturing of the second real-time view includes a second illumination of the subject, wherein the second illumination is different from the first illumination. In some embodiments, the first illumination has a first wavelength, and the second illumination has a second wavelength, wherein the second wavelength is different from the first wavelength. In some embodiments, the first illumination has a first intensity, and the second illumination has a second intensity, wherein the second intensity is different from the first intensity. In some embodiments, the first illumination has a first temporal modulation, and the second illumination has a second temporal modulation, wherein the second temporal modulation is different from the first temporal modulation.

In some embodiments, the capturing of the second real-time view includes application of a noise filtering algorithm or a noise averaging algorithm.

In some embodiments, the camera has a resolution. The recording of the first real-time view includes recording using the camera, wherein the resolution is a first resolution. The capturing of the second real-time view includes capturing using the camera, wherein the resolution is a second resolution. The method further includes altering the resolution from the first resolution to the second resolution based on the trigger, wherein the second resolution is higher than the first resolution.

In some embodiments, the camera has a field of view. The recording of the first real-time view includes recording using the camera, wherein the field of view is a first field of view. The capturing of the second real-time view includes capturing using the camera, wherein the field of view is a second field of view. The method further includes modifying the field of view from the first field of view to the second field of view based on the trigger, wherein the second field of view is smaller than the first field of view.

In some embodiments, the method further includes turning off a light directed at the subject based on the trigger. In some embodiments, the method further includes taking an X-ray image, a near-infrared image, or a radioisotope image based on the trigger.

In some embodiments, the monitoring includes registering a presence or an absence of an operator command. In some embodiments, the monitoring includes registering an acceleration of the sample or an acceleration of the camera. In some embodiments, the monitoring includes registering a difference between sequential frames of the first real-time view.

In some embodiments, the subject is a biological sample. In some embodiments, the biological sample is an in vivo sample. In some embodiments, the biological sample is an ex vivo sample. In some embodiments, the biological sample is from a mammalian subject. In some embodiments, the biological sample comprises a tumor.

Also provided is a machine-readable non-transitory medium embodying information indicative of instructions for causing the computer processor to perform operations for presenting images. The operations include recording using a camera a first real-time view of a subject. The camera has a camera location and a camera orientation, and the subject has a subject location and a subject orientation. The camera has a frame frequency, and the frame frequency is a first frame frequency. The operations further include rendering for display the first real-time view. The operations further include changing the camera location or the camera orientation or the subject location or the subject orientation in response to an operator command. The operations further include monitoring a rate of movement in response to the operator command. The operations further include sending a trigger to the camera based upon the rate of movement descending below a target rate. The operations further include switching the frame frequency from the first frame frequency to a second frame frequency based on the trigger, wherein the second frame frequency is less than the first frame frequency. The operations further include capturing using the camera a second real-time view of the subject, wherein the frame frequency of the camera is the second frame frequency, thereby increasing an amount of light collected in each frame. The operations further include outputting for display the second real-time view.

Also provided is a computer system for presenting images. The system includes at least one processor, and a memory operatively coupled with the at least one processor. The at least one processor executes instructions from the memory including program code for recording using a camera a first real-time view of a subject. The camera has a camera location and a camera orientation, and the subject has a subject location and a subject orientation. The camera has a frame frequency, and the frame frequency is a first frame frequency. The instructions further include program code for rendering for display the first real-time view. The instructions further include program code for changing the camera location or the camera orientation or the subject location or the subject orientation in response to an operator command. The instructions further include program code for monitoring a rate of movement in response to the operator command. The instructions further include program code for sending a trigger to the camera based upon the rate of movement descending below a target rate. The instructions further include program code for switching the frame frequency from the first frame frequency to a second frame frequency based on the trigger, wherein the second frame frequency is less than the first frame frequency. The instructions further include program code for capturing using the camera a second real-time view of the subject, wherein the frame frequency of the camera is the second frame frequency, thereby increasing an amount of light collected in each frame. The instructions further include program code for outputting for display the second real-time view.

DETAILED DESCRIPTION

Embodiments of the present invention relate in part to motion-adaptive switching of imaging functions, such as those, for example, used for surgical or biopsy imaging. The provided methods and systems can monitor for changes in motion, and responsively enhance or modify real-time images being captured or rendered for display. This can be accomplished by analyzing user control behaviors to determine when and how to optimize imaging results, while simultaneously responding to inputs from the user who is interactively directing a viewing motion around areas of interest. In brief, the user can use motion control to direct real-time 3-D imaging of a sample. The motion-adaptive imaging can then maintain a real-time, high-speed preview as the image is in motion, while automatically switching to an enhanced functional image when the image is relatively stationary. Because the imaging needs during movement and when stationary are often different, or even contradictory, the ability to automatically detect and respond to changes in motion is a valuable feature of the provided imaging methods and systems.

In many medical imaging applications, it can be beneficial to have an accurate and responsive interactive real-time view of a subject that an operator can use as a navigational guide for examining the subject. It can also be beneficial to have enhanced images of the subject that the operator can use to collect more detailed information related to a view of the subject once navigated to. Often, the qualities of such an enhanced image that make it useful for closer investigations also make the enhanced image poor for use in real-time navigation. For this reason, the switching between different imaging functions can be helpful. In this way, for example, when the movement of a real-time view has substantially stopped, functional imaging parameters or functional imaging channels can be switched on as enhancements to provide additional information such as enhanced imaging quality, longer integration for better sensitivity, additional imaging modalities, X-ray shots, overlapping of channels, filtering applications, color changes, adding computational results, and augmented information. The methods and systems can therefore be particularly helpful in identifying and characterizing areas of interest in real-time to assist in the localization of disease tissue in either a surgical suite or a pathology lab.

Figure 1:
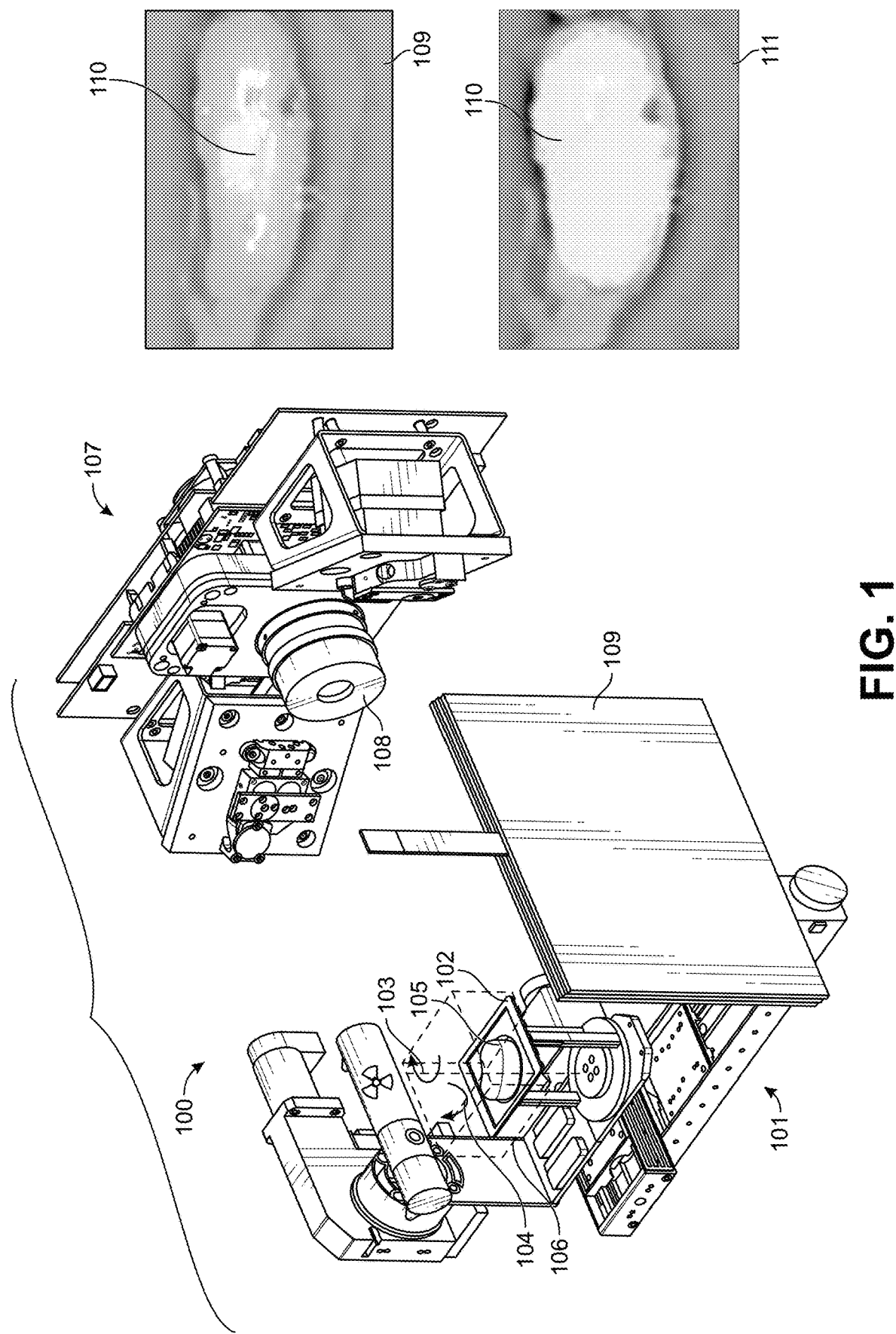
FIG. 1 is an illustration of an imaging system in accordance with an embodiment.

FIG. 1 illustrates one embodiment as a descriptive example. Shown is a sample positioning module 101 that includes an imaging stage 102. The imaging stage has a first rotational axis 103 and a second rotational axis 104. A biological sample 105 is shown being supported by the imaging stage. The biological sample is within an imaging volume 106 proximate to the imaging stage. Also shown is an optical imaging module 107 that includes a camera 108 configured to have a depth of focus within the imaging volume. The camera records a first real-time view 109 of the biological sample using a first frame rate frequency, and the first real-time view is rendered for display as shown. While the camera is recording with the first frame rate frequency, the sensitivity of the camera to faint signals, such as those of the fluorescent region 110 of the biological sample, is low.

The rotatable imaging stage 102 supporting the biological sample 105 is equipped with rotational motors to control the view angle and position of the sample within the imaging volume 106. By rotating a sample in two degrees of freedom 103, 104, the stage can allow the imager 107 to efficiently provide a substantially full-rotation 3D image. A first rotational axis can, for example, provide nearly 360-degree movement along the z-axis (roll) relative to the sample. A second rotational axis can, for example, tilt along the y-axis (pitch) for imaging at different perspectives. Tilting of the sample stage also can allow projection views from the top and the bottom of the sample via a transparent window. In some embodiments, the rotational imaging stage can also be moved in an X-Y plane to allow for the registration of the sample to the center of the imaging volume.

While the rotational stage 102 is in motion above a selected target motion rate, the camera 108 records the first real-time view 109 of the biological sample 105 using a first frame rate frequency. When the motion rate of the rotational stage descends below this target rate, a trigger is sent to the camera, and the frame frequency of the camera is switched from the first frame frequency to a second, lower frame frequency. The camera then captures a second real-time view 111 of the biological sample. As a result of the lower frame frequency used to capture and output this second real-time view, the amount of light collected in each frame is increased, and the sensitivity to the faint signals of the fluorescent region 110 is increased. Accordingly, the intensity of the perceived fluorescent signal is greater in the second real-time view than in the first real-time view.

The camera or imager can be configured to have any functional lens assembly, focal length, and exposure control sufficient to record the first real-time view of the subject. The camera or imager can record the first real-time view using an electronic image sensor. The camera or imager can include a charged coupled device (CCD) and/or a complementary metal-oxide-semiconductor (CMOS) sensor. In some embodiments, the first real-time view is monochromatic. In some embodiments, the first real-time view includes two or more colors. The camera can have an actively or passively cooled heat exchanger to maintain imaging sensors at low temperatures. The cooling can prevent optical background noise such as darkness or blooming. Exemplary camera and optical components are described in U.S. Pat. Nos. 7,286,232, 8,220,415, and 8,851,017.

The first and second real-time views represent depictions of the subject as seen from the viewpoint, such that there is minimal lag between the time of recording, capturing, or photographing the subject, and the time of rendering or outputting the views for display. The lag can be less than 5 seconds, less than 4 seconds, less than 3 seconds, less than 2 seconds, less than 1 second, less than 900 milliseconds, less than 800 milliseconds, less than 700 milliseconds, less than 600 milliseconds, less than 500 milliseconds, less than 400 milliseconds, less than 300 milliseconds, less than 200 milliseconds, or less than 100 milliseconds.

The camera used to record, capture, or photograph the real-time views of the subject has a frame frequency. The frame frequency can be at least 1 frame per second, at least 4 frames per second, at least 8 frames per second, at least 16 frames per second, at least 24 frames per second, at least 25 frames per second, at least 30 frames per second, at least 48 frames per second, at least 50 frames per second, at least 60 frames per second, at least 72 frames per second, at least 90 frames per second, at least 100 frames per second, at least 120 frames per second, at least 144 frames per second, or at least 240 frames per second. The frame frequency can be less than 1 frame per second. The frame frequency can be a relatively high frame frequency, sometimes referred to as a video rate. Typically, video rates are greater than or equal to 16 frames per second, with higher rates providing a smoother perception of motion.

The rendered or output real-time views for display can be identical to images recorded, captured, or photographed using the camera. The rendered or output real-time views can be constructions based on information in the recorded, captured, or photographed images. The rendered or output real-time views can contain images or information collected with one channel or modality. The rendered or output real-time views can overlay images or information collected with two or more channels or modalities. As a non-limiting example, a rendered image can overlay reflected light information showing a visible light view of the subject and X-ray information showing locations of radiodense regions within the biological sample. Typically, when a rendered image overlays images or information from multiple channels, modalities, or models, the models are co-registered in three-dimensional space so that the image presents information for each modality as seen from a single viewpoint.

The subject can be any person, animal, plant, or object to be imaged. The subject can be a biological sample. In some embodiments, the biological sample is one or more organisms. The biological subject can be one or more microscopic organisms. The biological sample can be a plant. The biological sample can be an animal. The biological sample can be a mammal. The biological sample can be a human. In some embodiments, the biological sample is a tissue, organ, or other subsection of an organism.

The biological sample can be an in vivo sample that is part or all of one or more living organisms. The biological sample can be an individual living microorganism. The biological sample can be a community of two or more living microorganisms. The biological sample can a living plant or animal. The biological sample can be a living mammal. The biological sample can be a living human. The biological sample can be a tissue, organ, or other subsection of a living human. In some embodiments, the biological sample is a region of an animal or human undergoing a surgical or other medical operation or analysis.

The biological sample can be an ex vivo sample of a tissue, organ, or other subsection removed from a plant or animal. The biological sample can be a tissue, organ, or other subsection removed from a mammal. The biological sample can be a tissue, organ, or other subsection removed from a human. In some embodiments, the biological sample is a resected human tissue sample. In some embodiments, the biological sample is a biopsy sample extracted from a human.

The biological sample can be of a mammalian subject. The mammalian subject can be, for example, rodent, canine, feline, equine, ovine, porcine, or a primate. The mammalian subject can be human.

The subject can be a patient suffering from a disease. In some embodiments, the subject is a cancer patient. In certain aspects, the biological sample comprises a tumor, such as tumor tissue or cells. In certain aspects, the biological sample comprises a peripheral biopsy of a tissue sample previously removed. In another aspect, the biological sample is tumor tissue such as a breast core biopsy. The biological sample size can be as small as a tissue slice.

The subject and the camera each have a location and an orientation. Typically, the camera is oriented such that it is pointing towards the subject, and the camera is located such that the subject is within the focal length of the camera. In some embodiments, as shown in FIG. 1, the orientation of the subject can be changed. In some embodiments, the location of the subject can be changed. In some embodiments, the orientation and/or location of the camera can change. By changing one or more of the locations and/or orientations of the subject and/or camera, real-time views of different areas of the subject can be captured, recorded, or photographed from multiple viewpoints.

The provided methods and systems can be applied, for example, to a cabinet biopsy imager or an image-guided surgical system. The changing of the location or orientation of the subject can occur when the subject is, for example, held on a sample stage that is interactively moved for 3D biopsy imaging. When the subject is a patient or a region of a patient within an operating room with an external or endoscopic imager, it is more likely that the subject will remain relatively stationary while the camera location or orientation is changed. In one example, a camera on a moving arm can providing different view angles at a wound bed. In another example, a camera can be used with a robotic image-guided surgical system. In each of these cases, the changing positions and orientations are used to enable 3D imaging of the subject.

3D imaging is a broadly-used common term representing the addition of depth perception to 2D images, including those from clinical areas such as computed tomography (CT), magnetic resonance imaging (MRI), and ultrasonography (Kopans (2014) *Amer. J. Roentgenology* 202:299; Ciatto et al. (2013) *Lancet Oncology* 14:583; Karatas and Toy (2014) *Eur. J. Dentistry* 8:132). It has also been applied in biomedical spaces such as those of microscopy, photoacoustic imaging, optical coherence tomography, spectroscopic imaging, and near-infrared imaging. In imaging and filming industries particular for entertainment purposes, 3D imaging has been well-known as a technique for displaying depth perception in projected images in movie theaters or other viewing environments.

A variety of imaging techniques have been termed as "3D." In some cases, 3D images can be produced through holography, which records a light field through an interference pattern and re-produces a spatial distribution of the light field in three dimensions. For a variety of tomographic methods, 3D imaging refers to the regeneration of the geometrical information of a subject via computing algorithms and calculations based on recorded data. 3D images can also simply be a stacking of optically sectioned X-Y 2D views, such as Z-stacking of images from confocal microscopy. Frequently, 3D images are produced using a stereoscopic effect by re-creating binocular vision to both left and right eyes at the same time to create the perception of 3D depth of an image. Such 3D imaging is often applied to movies, gaming, and entertainment applications. Through imaging reconstruction technologies, 3D images can be the computed representation of a subject formed in a computer-generated model based on either multiple real images or created virtual content. Such technologies have been used, for example, in the fields of virtual reality, mixed reality, and augmented reality. In photography, 3D pictures and 3D videos can be panoramic images obtained by recording views surrounding an observer by up to 360 degrees. 3D images can also offer only a sectional view of a part of an object, rather than a visualization of the full object. This is particularly the case in optical coherence tomography (OCT), scanning microscopy, and photoacoustic microscopy, where imaging depth and scanning coverage is very limited in its ability to capture the full view of a large subject.

As used herein, 3D imaging refers to the multi-angle visualization of a subject. The dynamic viewing from different angles or a collection of different view perspectives of an object gives the perception of depth, geometry, dimensions, features, and location of the subject. The imaging and dynamic viewing in multi-angles and orientations enables a 3D perception, not appreciated by traditional 2D representations via a static picture or a static view angle.

Figure 2:
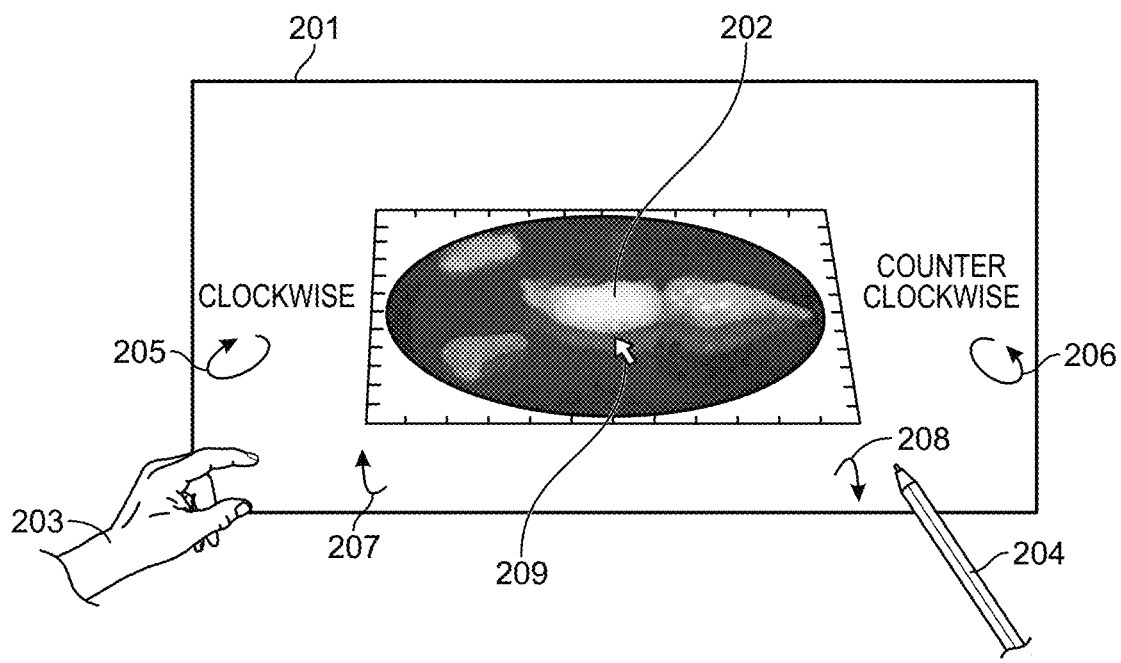
FIG. 2 is an illustration of methods for entering interactive motion commands in accordance with an embodiment.

FIG. 2 illustrates examples of interactive motion controls for changing the location and/or orientation of the subject and/or camera. Shown is a display 201 showing a real-time view of a subject 202. In some embodiments, operator commands to change a location or orientation are entered by touching the screen with a finger 203 or a device such as a touch pen 204. The touch commands can include pressing areas of the display showing virtual buttons 205, 206 for rotating the view in opposite directions about a first axis, and virtual buttons 207,208 for rotating the view in opposite directions about a second axis that is orthogonal to the first axis. The touching commands can include swiping, pinching, or spreading gestures to change the view by rotating, zooming, or panning. In some embodiments, operator commands to change a location or orientation include moving a cursor 209 on the display by using physical buttons, a computer mouse, a scroll ball, a control stick, switches, or a handheld controller. Operator commands for movement can also be entered using waving gestures, voice activation, or accelerometers.

The rate of movement of one or both of the subject and the camera can be monitored by registering the occurrence of operator commands. The rate of movement can be monitored by registering the presence or the absence of operator commands. In some embodiments, the movement slows or halts when an operator stops inputting a command for rotating, panning, or zooming the real-time view. In some embodiments the movement slows or halts when an operator inputs a command for slowing or halting a rotating, panning, or zooming of the real-time view. In some embodiments, the movement quickens or begins when an operator starts inputting a command for rotating, panning, or zooming the real-time view. In some embodiments the movement quickens or begins when an operator stops inputting a command for slowing or halting a rotating, panning, or zooming of the real-time view.

The rate of movement of one or both of the subject and the camera can be monitored by registering the acceleration of the subject and camera, respectively. In some embodiments, the camera includes a positioning system or one or more accelerometers that measure the location and movement rate of the camera. In some embodiments, the camera is connected to a support system such as, for example, an arm, that includes a positioning system or one or more accelerometers that measure the location and movement rate of the camera. In some embodiments, the subject is connected to an imaging platform, such as, for example, a rotational stage, that includes a positioning system or one or more accelerometers that measure the location and movement rate of the subject.

The rate of movement of one or both of the subject and the camera can be monitored by registering changes between two or more frames of the real-time view. In some embodiments, the rate of movement of one or both of the subject and the camera is monitored by registering a difference between sequential frames of the real-time view. The registering of changes between frames of the real-time view can be accomplished with any algorithm suitable for video frame comparison or matching. In some embodiments, the rate of movement is monitored by applying a block-matching algorithm, a phase correlation algorithm, a pixel recursive algorithm, an optical flow algorithm, or a corner detection algorithm.

A trigger can be sent to the camera when the monitored rate of movement of one or both of the subject and the camera descends below a target rate. The target rate can be expressed as a target degree of movement occurring in a target period of time. The target degree of movement can be, for example, 25%, 20%, 15%, 10%, 5%, 4%, 3%, 2%, or 1%. The target period of time can be, for example, 5 seconds, 4.5 seconds, 4 seconds, 3.5 seconds, 3 seconds, 2.5 seconds, 2 seconds, 1.5 seconds, 1 second, or 0.5 seconds. In some embodiments, the target rate of movement is 15% in 1.5 seconds. Upon receiving the trigger signal, the camera switches to a motion-adaptive imaging function. In some embodiments, the camera switches its frame frequency from a first frame frequency to a lower second frame frequency based on the trigger.

Figure 3:
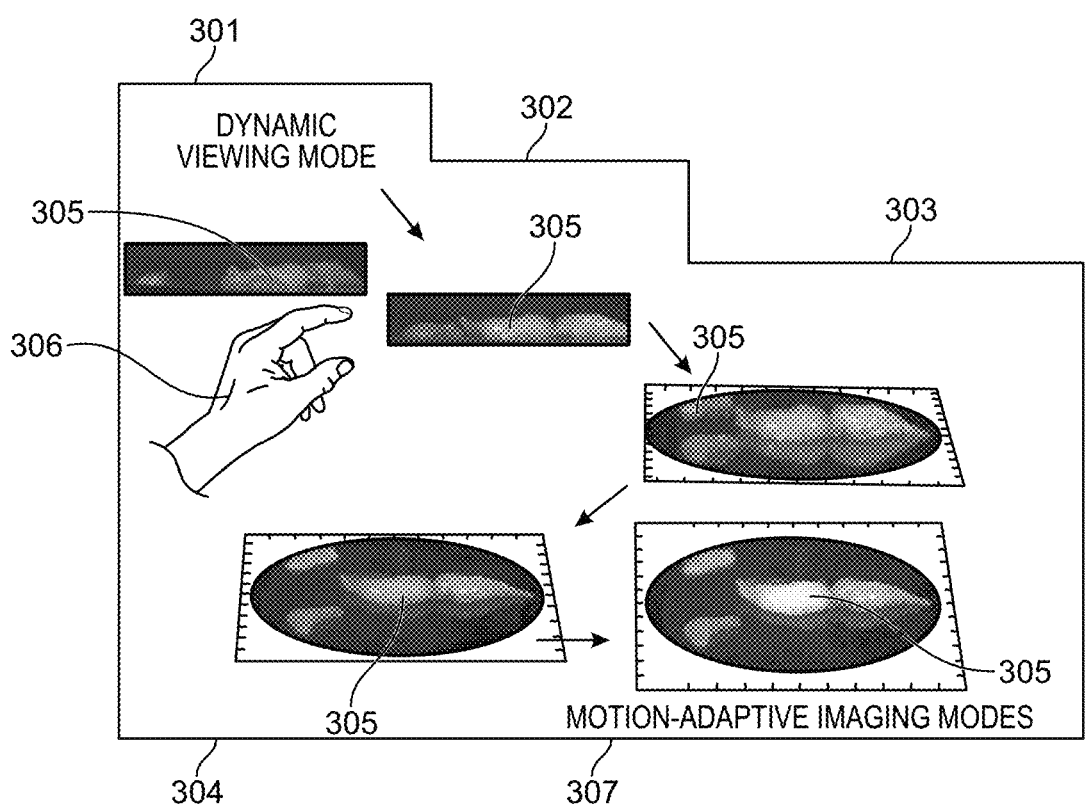
FIG. 3 is an illustration of motion-adaptive images rendered for display in accordance with an embodiment.

FIG. 3 illustrates an embodiment in which touch gestures are used to enter operator commands for moving the subject or camera, and an adaptive imaging mode increases the amount of light collected in each frame in response to the rate of movement dropping below a target rate. Shown are a series of four images 301, 302, 303, 304 from a real-time view of a subject 305. As an operator enters commands with touch gestures 306, the camera or subject are moved such that the real-time view changes from the first image 301 to the second 302, third 303, and then fourth image 304, presenting different viewpoints of the subject in the 3D imaging visualization. The rate of movement in response to the operator commands is monitored by any of the techniques discussed above. When the rate of movement descends below a target rate, a trigger is sent to the camera, and the frame frequency of the camera is changed to a higher frame frequency. Because of this higher frame frequency associated with the motion-adaptive imaging function, the camera collects more light in each frame, and the resulting fifth image 307 shows a stronger response to faint fluorescence signals emitting from the subject.

In some embodiments, a pause of motion input (or a gesture, or voice, or release of pressure on the touch screen, or increase of pressure on the screen, or a prolonged holding on the screen) at an area of interest indicates the expectation of higher sensitivity imaging to interrogate the disease tissue distribution in details. The computer then responsively triggers the adaptive imaging functions. The changes to the camera in response to the trigger signal are not limited to those affecting frame frequency rate, and can also include changes to imaging modes, channels, speeds, resolutions, or sensitivities. The changes can also include adjustments to the illumination of the subject, or to the processing of recorded, captured, or photographed information. For example, the motion-adaptive imaging function of the camera can include one or more of different integration times of imaging pixels on the image sensor, filtering algorithms, noise suppression algorithms, or boosts to the signal to noise ratio. Other changes in the motion-adaptive imaging function can include manipulating the image to show, for example, different colors, contrasts, or overlaid information. The motion-adaptive imaging function can add another imaging modality displayed in an overlaid fashion. In some embodiments, the switch to a motion-adaptive imaging function represents a shift from a high speed preview mode to a high-performance, high-sensitivity mode, with imaging parameters selected to improve or optimize each mode independently.

Figure 4:
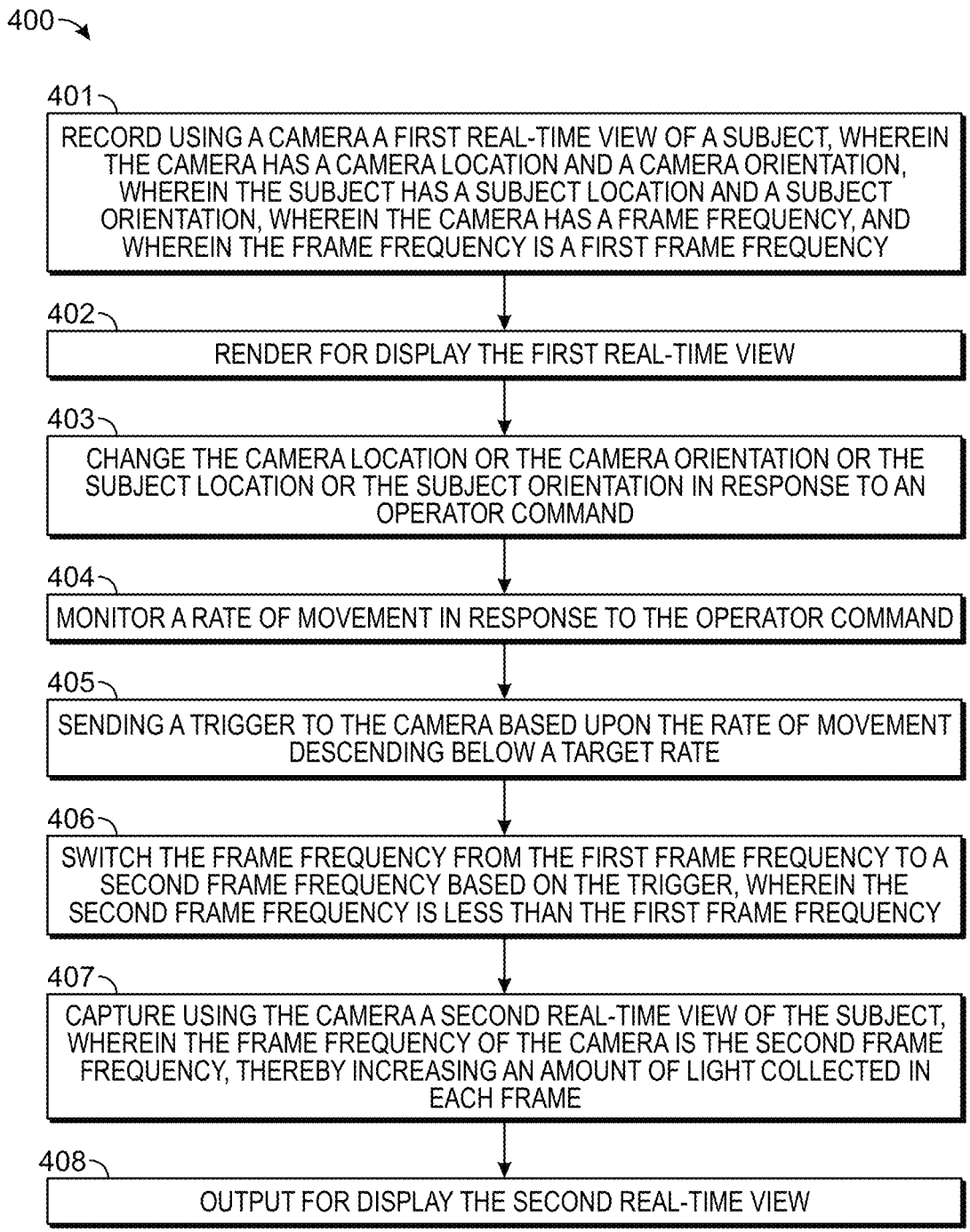
FIG. 4 is a flowchart of a process for detecting and presenting faint signals from a real-time interactive imager in accordance with an embodiment.

FIG. 4 presents a flowchart of a process 400 for detecting and presenting faint signals from a real-time interactive imager. In operation 401, a first real-time view of a subject is recorded using a camera, wherein the camera has a camera location and a camera orientation, wherein the subject has a subject location and a subject orientation, wherein the camera has a frame frequency, and wherein the frame frequency is a first frame frequency. In operation 402, a first real-time view is rendered for display. In operation 403, the camera location or the camera orientation or the subject location or the subject orientation is changed in response to an operator command. In operation, 404, a rate of movement in response to the operator command is monitored. In operation 405, a trigger is sent to the camera based upon the rate of movement descending below a target rate. In operation 406, the frame frequency is switched from the first frame frequency to a second frame frequency based on the trigger, wherein the second frame frequency is less than the first frame frequency. In operation 407, a second real-time view of the subject is captured using the camera, wherein the frame frequency of the camera is the second frame frequency, thereby increasing an amount of light collected in each frame. In operation 408, the second real-time view is output for display.

The camera can be a fluorescence camera configured to capture fluorescence images of the subject upon excitation of the subject by a fluorescence excitation light source. The fluorescence excitation light source can be any device configured to emit electromagnetic radiation at an excitation wavelength capable of exciting a fluorescent material within the imaging volume. The fluorescent material can comprise a fluorophore or fluorescent dye. The fluorescence excitation light source can be configured to illuminate the imaging volume, and any sample within, with radiation comprising this excitation wavelength. In some embodiments, the fluorescence excitation light source emits near-infrared light. In certain aspects, the illumination of the subject with near-infrared light is performed at one or more wavelengths of from about 650 nm to about 1400 nm. These wavelengths include, for example, about 700, 725, 750, 775, 800, 825, 850, 875, 900, 910, 920, 930, 940, 950, 960, 970, 980, 990, 1000, 1100, 1200, 1300, and 1400 nm. Sometimes these wavelengths are referred to as being in the NIR-I (between 750 and 1060 nm) and NIR-II (between 1000 nm and 1700 nm) wavelength regions.

Fluorophore methods utilize molecules that absorb light of one wavelength and emit light of a different wavelength. To utilize a visible image in combination with a fluorophore (e.g., an infrared or near-infrared fluorophore), care should be taken to ensure that the spectra of light variously absorbed, reflected, and emitted do not significantly overlap so as to confound differentiation of the components from each other and differentiation of the components from endogenous tissue material. Filter sets can be used in the optical system to isolate excitation wavelengths with optimized emission collection for corresponding imaging agents.

In certain aspects, the subject comprises a fluorescent dye. In one aspect, the fluorescent group is a near-infrared (NIR) fluorophore that emits in the range of between about 650 to about 1400 nm. Use of near-infrared fluorescence technology can be advantageous as it substantially eliminates or reduces background from auto fluorescence of tissue. Another benefit to near-IR fluorescent technology is that scattered light from the excitation source is greatly reduced since the scattering intensity is proportional to the inverse fourth power of the wavelength. Low background fluorescence and low scattering result in a high signal to noise ratio, which is essential for highly sensitive detection. Furthermore, the optically transparent window in the near-IR region (650 nm to 990 nm) or NIR-II region (between about 1000 nm and 1400) in biological tissue makes NIR fluorescence a valuable technology for imaging and subcellular detection applications that require the transmission of light through biological components.

In certain aspects, the fluorescent group is preferably selected form the group consisting of IRDYE® 800RS, IRDYE® 800CW, IRDYE® 800, ALEXA FLUOR® 660, ALEXA FLUOR® 680, ALEXA FLUOR® 700, ALEXA FLUOR® 750, ALEXA FLUOR® 790, Cy5, Cy5.5, Cy7, DY 676, DY680, DY682, and DY780 molecular marker. In certain aspects, the near infrared group is IRDYE® 800CW, IRDYE® 800, IRDYE® 700DX, IRDYE® 700, or Dynomic DY676 molecular marker.

In certain aspects, a fluorescent dye is contacted with a biological sample prior to excising the biological sample from the subject. For example, the dye can be injected or administered to the subject prior to surgery or after surgery.

In certain aspects, the dye is conjugated to an antibody, ligand, or targeting moiety or molecule having an affinity to a tumor or recognizes a tumor antigen. In certain aspects, the fluorescent dye comprises a targeting moiety. In one aspect, the surgeon "paints" the tumor with the dye. In certain aspects, the fluorescent dye is contacted with the biological sample after excising the biological sample from the subject. In this manner, dye can be contacted to the tissue at the margins.

In some aspects, the targeting molecule or moiety is an antibody that binds an antigen such as a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, or an osteosarcoma cell surface antigen.

The camera can be a reflected light camera configured to capture white light reflected by the subject. The camera can be a gray-scale or true-color imager. The camera can be a multichannel imager with a reflective light mode with at least one fluorescence channel. The imager can also be combined with X-ray imaging. The motion-adaptive method can also be used on an X-ray only multi-angle, multi-dimensional imager for radiography of a sample The first real-time view and the second real-time view can be recorded, captured, or photographed with the same camera. The first real-time view and the second real-time view can be recorded, captured, or photographed with different cameras. Each of the first and second real-time views can be recorded with multiple cameras. In some embodiments, a reflected white light camera with a first frame frequency is used to record the first real-time view, and a fluorescence camera with a second frame frequency is used to capture the second real-time view.

Figure 5:
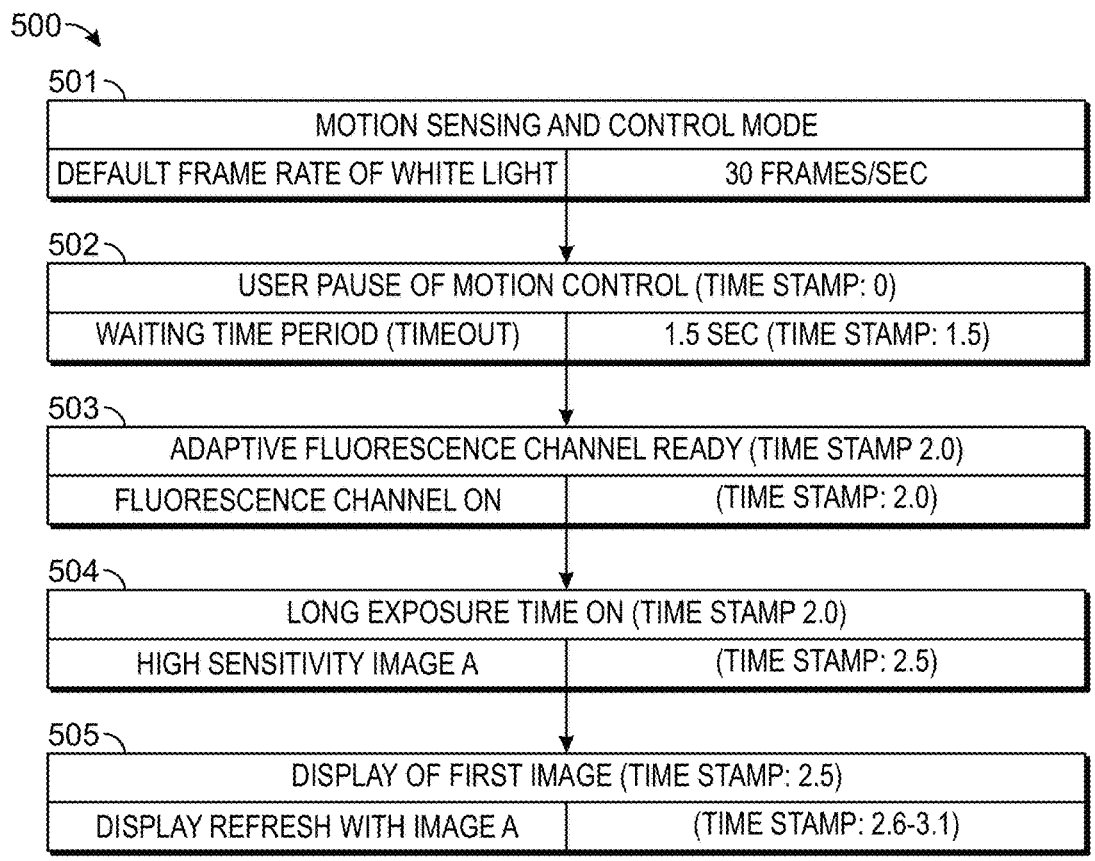
FIG. 5 is a time course for the use of a single camera to switch from a reflected light preview to a high sensitivity fluorescence mode in accordance with an embodiment.

FIG. 5 presents an exemplary time course for a process 500 using a single camera to adaptively switch from a reflected light preview mode to a fluorescence mode characterized by a long exposure time of the camera image sensor. During the times of the motion sensing and control mode 501, the camera records a first real-time view of a subject using reflected white light and a default frame rate of 30 frames per second. At time event 502, the user pauses motion control, and the method enters a 1.5-second waiting time period to determine if the monitored rate of movement descends below a target rate. At time events 503 and 504, the camera is switched to the motion-adaptive imaging function, with a fluorescence channel of the camera turned on, and the exposure time increased. At time event 505, the camera begins capturing the second real-time view of the subject using fluorescence and the second frame rate characteristic of the increased exposure time.

Figure 6:
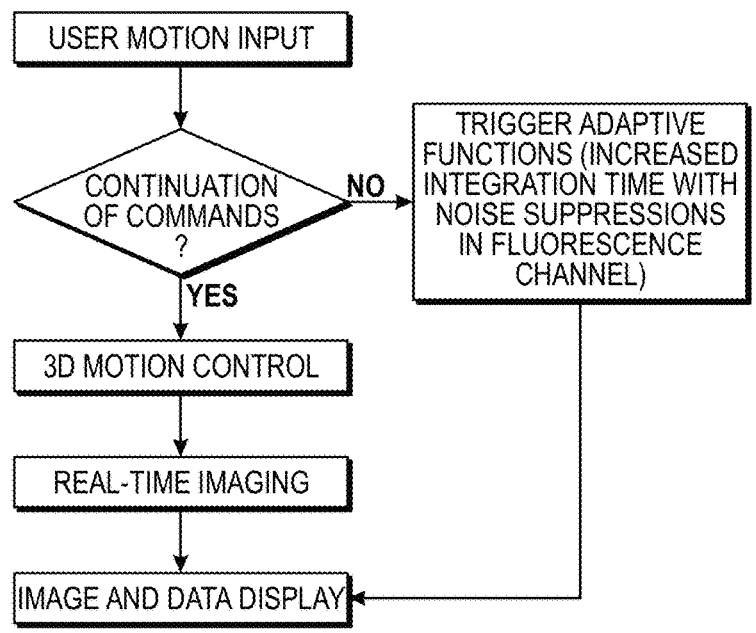
FIG. 6 is a flowchart of an adaptive imaging process in accordance with an embodiment.

FIG. 6 presents one workflow of an adaptive imaging process. A user inputs commands for motion interactively to the imaging system. The system receives these interactive controls and provides 3D movement for real-time imaging. The interactive motion control commands are entered via touching the screen or other computer input methods such as with the use of a computer mouse, a control stick, a scroll ball, switches, or a handheld controller. As these commands continue, real-time images, typically at a video rate, are continuously rendered for display. Once the system recognizes a discontinuation of command inputs within a default period of time, or the release of the touch on the screen, the system responsively triggers the adaptive imaging functions. These adaptive functions can include increasing the integration time of pixels of the image sensor and applying noise suppression algorithms. The result of these adaptive functions is the enhancement of imaging sensitivity in the fluorescence channel which can be overlaid with images from a reflective channel or other imaging modalities. The user will then observe an increase in signal level due to the higher image sensitivity at the fluorescence channel so that localization of disease tissue can be performed.

In addition to reflected white light imaging and fluorescence imaging, other imaging modalities can be used with the provided methods and systems. For example, X-ray, near-infrared, radioisotope, or ultrasound images can be captured based on the trigger signal. X-ray information can be used to show locations of radiodense regions within the subject or biological sample. The motion-adaptive imaging methods can then be used with an X-ray biopsy imager to provide responsive shots of, for example, a lumpectomy samples at multiple user-selected angles.

X-ray images can be produced by exposing the subject to X-ray irradiation from an X-ray source, and recording the X-rays with an X-ray imager. The X-ray source can be any artificial X-ray source configured to irradiate the imaging volume with X-rays. In some embodiments, the X-ray source is an X-ray tube. The X-ray tube can comprise a rotating anode tube. In some embodiments, the X-ray source is a solid-anode microfocus X-ray tube or a metal-jet-anode microfocus X-ray tube.

The X-ray imager can be any device configured to measure the properties of X-rays exiting the image volume. The X-ray imager can comprise, for example, one or more of a sensitized photographic plate, sensitized photographic film, a photostimulable phosphor plate, a semiconductor or solid state detector, or a scintillator. In some embodiments, the X-ray imager comprises a scintillator. The scintillator can comprise any material that converts an X-ray photon to a visible light photon. The scintillator can comprise one or more organic or inorganic compounds. The scintillator compounds can comprise, for example, barium fluoride, calcium fluoride doped with europium, bismuth germinate, cadmium tungstate, cesium iodide doped with thallium, cesium iodide doped with sodium, undoped cesium iodide, gadolinium oxysulfide, lanthanum bromide doped with cerium, lanthanum chloride doped with cerium, lead tungstate, lutetium iodide, lutetium oxyorthosilicate, sodium iodide doped with thallium, yttrium aluminum garnet, zinc sulfide, or zinc tungstate. In some embodiments, the scintillator comprises sodium iodide, gadolinium oxysulfide, or cesium iodide.

In some embodiments, the X-ray imager is a an X-ray flat panel detector. The flat panel detector can comprise a scintillator material and a photodiode transistor array. The flat panel detector can further comprise one or more readout circuits. The flat panel detector can comprise a detection face and a display face on opposite sides of the detector from one another. The detection face can be directed towards the biological sample and the X-ray source so as to be contacted with X-rays generated by the X-ray source and passing through the imaging volume. The display face can be directed towards a camera so that an X-ray image displayed on the display face can be recorded using the camera. In some embodiments, the X-ray image is displayed on the display face by generating visible light that is recorded by a visible light camera configured to have a depth of focus that corresponds to the distance between the display face and the camera.

Ultrasonic images can be produced with an ultrasonic transducer array configured to detect ultrasound waves exiting the imaging volume and convert the waves into electrical signals. Energy pulses transmitted into the imaging volume can cause a biological sample within to absorb this timevarying energy, inducing the generation of acoustic waves that can be detected by the ultrasonic transducer array. Within the imaging volume, the ultrasonic transducer array is in contact with the biological sample via a coupling medium. The coupling medium can comprise water or gel to relay ultrasound waves. In some embodiments, the energy pulses are non-ionizing light pulses and the ultrasonic transducer array can be used to record a photoacoustic image. In some embodiments, the energy pulses are radio frequency pulses and the ultrasonic transducer array can be used to record a thermoacoustic image. In some embodiments, the energy pulses are ultrasonic pulses, and the ultrasonic transducer array can be used to record an ultrasound image.

Optical coherence tomography images can be produced with an interferometer configured for tomography of the biological sample within the imaging volume. In some embodiments, the interferometer is a Michelson interferometer. A camera can be configured to detect electromagnetic radiation emitted from the imaging volume for optical coherence tomography of the biological sample.

The motion-adaptive imaging functions can include one or more noise filtering or noise averaging processes. Any signal processing algorithm suitable for image noise reduction can be used with the provided methods and systems. The noise reduction algorithms can include, for example, chroma and luminescence noise separation, linear smoothing, anistropic diffusion, non-local averaging, or wavelet transformations.

Figure 7:
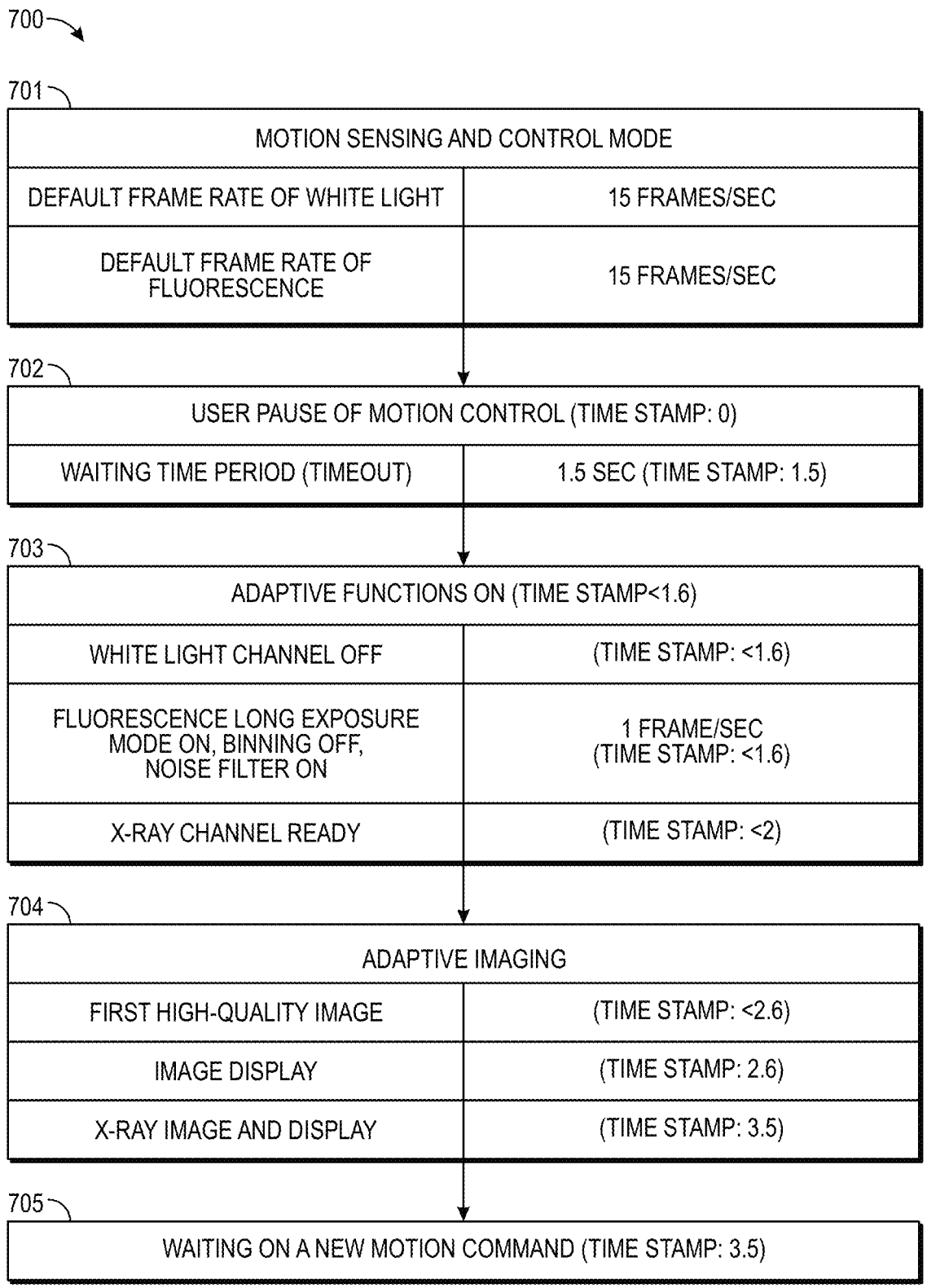
FIG. 7 is a time course for a multi-modal system with multiple motion-adaptive functions in accordance with an embodiment.

FIG. 7 presents an exemplary time course 700 for a multi-modal system that starts with both a white light and a fluorescence channel, and then adaptively switches on multiple functions. During the times of the motion sensing and control mode 701, the camera records a first real-time view of a subject using both reflected white light and fluorescence, each with a frame rate of 15 frames per second. During this time, the subject is illuminated with a high-frequency modulated illumination that alternates between white light and fluorescence excitation wavelengths. The collection of reflected white light and fluorescence emissions is through one or two cameras that can be synchronized with the illumination modulation. At time event 702, the user pauses motion control, and the method enters a 1.5-second waiting time period to determine if the monitored rate of movement descends below a target rate. At time event 703, the imaging system is switched to multiple motion-adaptive imaging functions. These include the turning off of the white light illumination channel, the switching of the fluorescence camera frame frequency to a lower frequency characteristic of a long exposure mode, the stopping of binning in the image processing of the camera, the starting of the application of a noise filtering algorithm, and the readying of an additional imaging modality for X-ray image capture. At time event 704, the fluorescence camera begins capturing the second real-time view of the subject using fluorescence and the second frame rate, and the X-ray imager records an X-ray image for display. At time event 705, the imaging system begins to wait for user entry of new motion commands.

Figure 8:
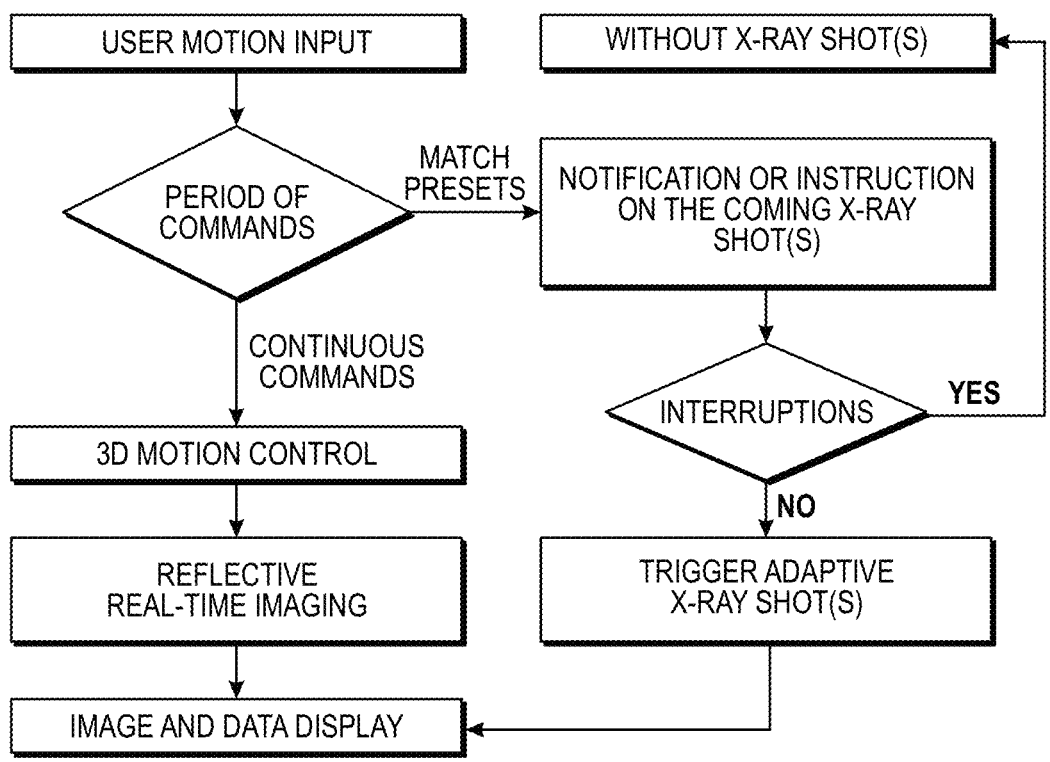
FIG. 8 is a flowchart of a motion-adaptive multi-angle X-ray imaging process in accordance with an embodiment.

FIG. 8 presents a workflow of a motion-adaptive multi-angle X-ray imaging process. A user inputs motion commands interactively to the imaging system. The system receives these commands and moves a sample stage to provide multi-dimensional movement for real-time reflective-light imaging in an imaging cabinet. Real-time images are rendered for display continuously to show the sample orientation inside the imaging cabinet. Once the system recognizes the movement rate has dropped such that a period of commands is reduced, the system triggers an X-ray imaging instruction that a user can interrupt. In the absence of interruption, an X-ray image is captured. The X-ray image can be output for presentation along with the real-time reflective view in the same overlaid image or separate images. The user can then continue the motion to re-orient the sample or take another X-ray shot.

The first and second real-time views of the subject recorded using standard and motion-adaptive imaging functions, respectively, can each contain one or more imaging modalities. In the case of two or more imaging modalities, the separate modalities can be rendered or output for display in overlaid or separate images. The imaging modalities can include reflected white light imaging, fluorescence imaging, X-ray imaging, near infra-red imaging, ultrasonic imaging, optical coherence tomography imaging, or others. The real-time views captured using the motion-adaptive functions can be overlaid with an image recorded using the standard imaging functions prior to the sending of the trigger to begin motion-adaptive imaging. In some embodiments, a reflected white light image of the subject recorded or photographed prior to the sending of the trigger is overlaid with the real-time view of the subject captured subsequent to the sending of the trigger.

The standard and motion-adaptive imaging functions can each include an illumination of the subject. The second illumination for the motion-adaptive imaging subsequent to the sending of the trigger can be different from the first illumination for the standard imaging prior to the sending of the trigger. The first and second illuminations, and the light received by cameras and imagers associated with the provided methods and systems, can include any wavelength of electromagnetic radiation. The illuminations can be provided by one or more illumination sources. Illumination sources can be mounted proximate to the imaging volume in order to illuminate the sample with white light, monochrome light, near-infrared light, fluorescence light, or other electromagnetic radiation. One or more white lights can be used to illuminate the imaging volume. In some embodiments, the illumination of the subject with visible light is performed at one or more wavelengths of about 380 nm to about 700 nm. These wavelengths include, for example, about 380, 390, 400, 425, 450, 475, 500, 525, 550, 575, 600, 625, 650, 675, or about 700 nm. These wavelengths can occur in combination, such as in broadband white light. In some embodiments illumination at one or more wavelengths is stopped by the switch to motion-adaptive imaging. In some embodiments, a light is turned off by the switch to motion-adaptive imaging.

The first and second illuminations can have similar or different intensities. The first and second illuminations can have similar or different temporal modulations. In some embodiments, an illumination can include both white light and fluorescence excitation light used to alternately illuminate the subject in a modulated fashion. The modulated electromagnetic radiations can differ in amplitude, phase, frequency, or polarization.

The first and second real-time views of the subject recorded using standard and motion-adaptive imaging functions, respectively, can have similar or different resolutions. The real-time views can have similar or different pixel resolutions, spatial resolutions, spectral resolutions, temporal resolutions, or radiometric resolutions. The first and second real-time views of the subject recorded using standard and motion-adaptive imaging functions, respectively, can have similar or different fields of view.

The devices and methods can utilize a computing apparatus that is programmed or otherwise configured to automate and/or regulate one or more steps of the methods or features of the devices provided herein. Some embodiments provide machine executable code in a non-transitory storage medium that, when executed by a computing apparatus, implements any of the methods or operates any of the devices described herein. In some embodiments, the computing apparatus operates one or more power sources, motors, and/or displays. A display can be used for review of the real-time views. The display can be a touch screen to receive interactive command inputs. The display can be a wireless device relaying the information wirelessly.

The terms "first", "second", "third", "fourth", and "fifth", and "sixth" when used herein with reference to images, views, frequencies, cameras, illuminations, wavelengths, intensities, modulations, resolutions, fields of view, axes, or other elements or properties are simply to more clearly distinguish the two or more elements or properties and unless stated otherwise are not intended to indicate order.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of detecting and presenting images, the method comprising:
   recording, using a fluorescence camera, a first view of a subject at a first frame frequency;
   photographing a reflected white light view of the subject with a second camera;
   rendering for displaying the first view;
   monitoring, using a processor, a rate of movement of the subject in the reflected white light view from the second camera;
   sending a trigger, using the processor, to the fluorescence camera based upon the rate of movement descending below a target rate;
   switching, using the processor, the first frame frequency to a second frame frequency based on the trigger, wherein the second frame frequency is lower than the first frame frequency;
   capturing, using the fluorescence camera, a second view of the subject at the second frame frequency, thereby increasing an amount of light collected in each frame; and
   outputting for displaying the second view.

2. The method of claim 1, wherein the outputting includes overlaying the reflected white light view of the subject over the second view of the subject, wherein the reflected white light view was photographed prior to the sending of the trigger.

3. The method of claim 1, further comprising:
   illuminating the subject with a first excitation light while recording the first view;
   switching the first excitation light to a second excitation light in response to the trigger; and
   illuminating the subject with a second excitation light while capturing the second view.

4. The method of claim 3, wherein the first excitation light has a first wavelength and the second excitation light has a second wavelength.

5. The method of claim 3, wherein the first excitation light has a first intensity and the second excitation light has a second intensity.

6. The method of claim 3, wherein the first excitation light has a first temporal modulation and the second excitation light has a second temporal modulation.

7. The method of claim 1, wherein the capturing of the second view includes an application of a noise filtering algorithm or a noise averaging algorithm.

8. The method of claim 1, wherein the fluorescence camera has a resolution, wherein the recording of the first view is at a first resolution, and the capturing of the second view is at a second resolution, and wherein the method further comprises:
   altering the resolution from the first resolution to the second resolution based on the trigger, wherein the second resolution is higher than the first resolution.

9. The method of claim 1, wherein the fluorescence camera has a field of view, wherein the recording of the first view is of a first field of view, and the capturing of the second view is of a second field of view, and wherein the method further comprises:
   modifying the field of view from the first field of view to the second field of view based on the trigger, wherein the second field of view is smaller than the first field of view.

10. The method of claim 1, further comprising:
    turning off a light source directed at the subject based on the trigger.

11. The method of claim 1, further comprising:
    taking an X-ray image, a near-infrared image, or a radioisotope image based on the trigger.

12. The method of claim 1, wherein the monitoring includes registering a presence or an absence of an operator command.

13. The method of claim 1, wherein the subject is a biological sample.

14. A machine-readable non-transitory medium embodying information indicative of instructions for causing a computer processor to perform operations for presenting images, the operations comprising:
    controlling a fluorescence camera to record a first view of a subject at a first frame frequency;
    controlling a second camera to photograph a reflected white light view of the subject;
    rendering for displaying the first view;
    monitoring a rate of movement of the subject in the reflected white light view from the second camera;
    sending a trigger to the fluorescence camera based upon the rate of movement descending below a target rate;
    switching the first frame frequency to a second frame frequency based on the trigger, wherein the second frame frequency is lower than the first frame frequency;
    controlling the fluorescence camera to capture a second view of the subject at the second frame frequency, thereby increasing an amount of light collected in each frame; and
    outputting for displaying the second view.

15. The medium of claim 14, wherein the operations further comprise:
    controlling a first excitation light to illuminate the subject while recording the first view;
    switching the first excitation light to a second excitation light in response to the trigger; and controlling a second excitation light to illuminate the subject while capturing the second view.

16. A computer system for presenting images, the system comprising:
at least one processor, and
a memory operatively coupled with the at least one processor, the at least one processor executing instructions from the memory, the memory comprising:
a) program code for controlling a fluorescence camera to record a first view of a subject at a first frame frequency; b) program code for controlling a second camera to photograph a reflected white light view of the subject;
c) program code for rendering for displaying the first view;
d) program code for monitoring a rate of movement of the subject in the reflected white light view from the second camera;
e) program code for sending a trigger to the fluorescence camera based upon the rate of movement descending below a target rate;
f) program code for switching the first frame frequency to a second frame frequency based on the trigger, wherein the second frame frequency is lower than the first frame frequency;
g) program code for controlling the fluorescence camera to capture a second view of the subject at the second frame frequency, thereby increasing an amount of light collected in each frame; and
h) program code for outputting for displaying the second view.

17. The computer system of claim 16, wherein the memory further comprises:
program code for controlling a first excitation light to illuminate the subject while recording the first view
program code for switching the first excitation light to a second excitation light in response to the trigger; and
program code for controlling a second excitation light to illuminate the subject while capturing the second view.

* * * * *